United States Patent [19]

van den Honert et al.

[11] Patent Number: 5,024,612

[45] Date of Patent: Jun. 18, 1991

[54] EXTERNAL EAR CANAL PRESSURE REGULATING DEVICE AND TINNITUS SUPPRESSION DEVICE

[75] Inventors: Christopher van den Honert, Maplewood; Paul H. Stypulkowski, North Oaks, both of Minn.

[73] Assignee: Minnesota Mining and Manufacturing Company, St. Paul, Minn.

[21] Appl. No.: 359,025

[22] Filed: May 30, 1989

Related U.S. Application Data

[63] Continuation-in-part of Ser. No. 286,744, Dec. 19, 1988.

[51] Int. Cl.$^5$ .............................................. A61F 11/00
[52] U.S. Cl. ................................................... 604/36
[58] Field of Search ................ 128/746, 897–898, 128/38, 40, 860–868; 604/27–28, 35–38, 54, 212–216

[56] References Cited

U.S. PATENT DOCUMENTS 3,683,929  8/1972  Holter .......................... 604/212 X

FOREIGN PATENT DOCUMENTS 0146247  2/1981  Fed. Rep. of Germany ...... 128/746

*Primary Examiner*—William E. Kamm
*Attorney, Agent, or Firm*—Donald M. Sell; Walter N. Kirn; William D. Bauer

[57] ABSTRACT

A tinnitus suppression device using an in-the-canal external ear canal pressure regulating device to alter the pressure of the fluid of the external ear canal interior of the pressure regulating device. The device has a body which can be inserted into the external ear canal and which seals the canal from ambient pressure. An adjustably sized body such as a collapsible bulbous portion or a bellows type wall provides a mechanism for altering the pressure in the canal. Either a valve or a mechanical displacement device maintains the pressure differential created.

23 Claims, 6 Drawing Sheets

EXTERNAL EAR CANAL PRESSURE REGULATING DEVICE AND TINNITUS SUPPRESSION DEVICE

RELATED APPLICATION

The present application is a continuation-in-part of U.S. Ser. No. 07/286,744, Stypulkowski, APPARATUS AND METHOD FOR SUPPRESSING TINNITUS, filed Dec. 19, 1988.

BACKGROUND OF THE INVENTION

The present invention relates generally to auditory prostheses and, more particularly, to auditory prostheses for use in the external ear canal.

Many individuals have suffered and currently do suffer from tinnitus. Tinnitus, simply defined, is the perception of sound in the ear which does not, in fact, exist, i. e., is not present in the external environment. These sounds typically may be characterized as a ringing, whistling, roaring or buzzing. Tinnitus has been reported to affect up to thirty percent (30%) of the United States population. Individuals with tinnitus may have symptoms ranging from mild to severe and ranging from chronic to intermittent. Several million people in the United States suffer debilitating tinnitus which interferes with everyday activities. In some cases, tinnitus can be chronic and severe, debilitating the individual.

Several attempts have been made in the past to mask or "cure" tinnitus. Some of these attempts have involved treating the tinnitus by the administration of drugs. An example of these attempts is disclosed in U.S. Pat. No. 4,735,968, Guth.

In some cases the tinnitus is so severe that drastic steps have been taken to eliminate the sensation. The symptom of tinnitus can be "cured" by a section of the VIIIth nerve in one ear, completely eliminating any sensation of hearing in that ear. An example of a drastic attempt to "cure" tinnitus is disclosed in U.S. Pat. No. 4,408,602, Nakajima.

Some prior attempts for suppressing tinnitus have involved the use of electrical stimulation.

An example of this type of electrical stimulation is described in the *ATA Newsletter*, Vol. 10, No. 1, American Tinnitus Association, pp. 1–4 (March 1985). Electrical stimulation, however does not actually suppress tinnitus but rather simply attempts to mask the existing tinnitus sound with another sound created by the electrical stimulus signal. The ultimate goal of electrical stimulation is to suppress tinnitus without adding any other sounds. In some cases this is possible with direct current (DC) electrical stimulation. However, direct electrical currents cause damage to biological tissue and thus, this method cannot be practiced chronically. In some other cases, the electrical stimulation adds, rather than subtracts, from the sound environment, but for some individuals this may be more pleasant than doing nothing since the tinnitus sound may be so disturbing.

A similar example of masking, in this case with acoustic stimulation is shown in U.S. Pat. No. 4,222,393, Hocks et al, Tinnitus Masker, which discloses a system in which a tinnitus patient is subjected to external sounds of differing pitches to determine the frequency of the perceived tinnitus sound and then provided with signals both above and below the determined frequency in order to mask the tinnitus. These systems do not eliminate or cure the tinnitus but merely superimpose another stimulus on top of the existing tinnitus sensation in an attempt to mask the perceived sensation.

In an article by B. Densert and O. Densert, "Overpressure in Treatment of Meniere's Disease", 92 *Laryngoscope* pp. 1285–1292 (November 1972), the Denserts described tests they conducted on patients suffering from Meniere's disease. It is to be pointed out that Meniere's Disease, sometimes referred to as cochlear hydrops, is a significantly different condition from tinnitus which accompanies a typical high frequency hearing loss. That is, Meniere's Disease tinnitus represents only a small portion of the tinnitus which exists in the general population. In some of the tests, they conducted local overpressure tests on the middle ear using a tube inserted through the tympanic membrane. In their tests they used a pressure increase upon which a low frequency sine wave was imposed. They require the sine wave oscillating pressure. The Denserts' main intention appears to be to treat patients with Meniere's disease. Since the main symptoms of Meniere's disease are hearing deficiency and vertigo, these are the symptoms which the Denserts have tested. In the question and answer period at the end of the presentation which resulted in this paper, in response to a question, they did say that they had had success in treating the tinnitus symptom.

Densert et al, in *PCT International Published Patent Application No. WO* 83/02556, An Apparatus for Influencing the Hydrodynamic System in the Inner of an Ear, describes an apparatus for treating Meniere's disease, which has primary symptoms of hearing deficiency and vertigo, with tinnitus being a secondary symptom. The apparatus is a large, stationary, office apparatus which, at certain treatment intervals, attempts to reduce the volume of the endolymph by introducing a fluctuating pressure upon the perilymphatic fluid. It is fundamental in the design of the apparatus that a patient would go to an office, be temporarily connected to the apparatus, undergo treatment and leave the office with the expectation that the changes in the endolymph would remain for a significant period of time. The pressures induced upon the perilymphatic fluid, in order to force a reduction in the volume of the endolymph, requires generating a static positive pressure level (during the treatment time period only) and generating a varying pressure level on top of the static positive pressure. The frequency of the varying pressure is described to be between 3 and 6 Hertz. Thus, the apparatus described in Densert et al PCT attempts to reduce the volume of the endolymph by temporarily inducing a fluctuating positive pressure on the endolymph in order to reduce the symptoms of Meniere's disease which have primary symptoms of hearing loss and vertigo and a secondary symptom of tinnitus.

European Patent Publication No. 0 266 474 A1, of Application No. 8650390.5, Procedure and Equipment for Treatment of Meniere's Disease, also by the Denserts, describes a very similar device. The apparatus requires the generation and transmission of complex pressure pulses in the fluid system of the inner ear in order to reduce the volume of the endolymph. As in the previous publications from the Denserts, a fluctuating, varying, or complex positive pressure is introduced to the inner ear in order to force fluid from the endolymph for the treatment of Meniere's disease, i. e., cochlear hydrops.

SUMMARY OF THE INVENTION

The present invention provides an auditory prosthesis which can be utilized in the external ear canal in order to modify the pressure existing in the external ear from ambient.

It has been found that an auditory prosthesis placed in the external ear canal and which provides for a modification from ambient of the pressure within the external ear canal can provide for the reduction, suppression or elimination of tinnitus.

The present invention provides a tinnitus suppression device adapted to be utilized in conjunction with a person having an auditory system with an external ear canal. The tinnitus suppression device has a body, sized and shaped for insertion into the external ear canal of the person. The body has an orifice allowing for the communication of fluids in and out of the external ear canal with the device in place within the external ear canal. The tinnitus suppression device also has a sealing mechanism coupled to the body for sealing for the external ear canal from ambient. Further, the tinnitus suppression device has a pressure mechanism incorporated within the body and operably coupled to the orifice of the body for creating a selected pressure to be applied to the external ear canal with the device in place. Thus, the tinnitus suppression device creates the selected pressure within the external ear canal suppressing the tinnitus.

Preferably the tinnitus suppression device also has a maintenance mechanism operably coupled to the orifice of the body for maintaining the selected pressure within the external canal with the body in place. Preferably the maintenance mechanism is a valve located within the orifice of the body. Preferably the selected pressure within the external ear canal has a lower absolute value than the value of ambient pressure. Preferably the valve is a one-way valve which only allows the fluid to pass from the external ear canal outwardly to ambient. Preferably the pressure mechanism comprises a bulbous portion of the body which when manually squeezed by the person lowers the volume of fluid present within the external ear canal and the body with the body in place and which when manually released lowers the pressure of the fluid still present in the external ear canal with respect to ambient. Preferably the pressure is lowered by approximately 500 decaPascals.

In an alternative embodiment, the tinnitus suppression device has an ear plug adapted to be placed in the external ear canal of the person, the ear plug having an orifice allowing for the communication of fluids to and from the external ear canal with the ear plug in place within the external ear canal and a pressure mechanism incorporated within the ear plug and operably coupled to the orifice of the ear plug for creating a selected pressure to be applied to the external ear canal with the ear plug in place.

In an alternative embodiment, the tinnitus suppression device has a sealing mechanism, sized and shaped for insertion into the external ear canal of the person, the sealing mechanism having an orifice allowing for the communication of fluids in and out of the external ear canal with the device in place within the external ear canal for sealing the external ear canal from ambient, a pressure mechanism incorporated within the device and coupled to the orifice of the sealing mechanism for creating a selected pressure to be applied to the external ear canal with the device in place and a maintenance mechanism operably coupled to the orifice for maintaining the selected pressure in the external canal.

The present invention also provides an external ear canal pressure regulating device adapted to be utilized in conjunction with the external ear canal of a person. The external ear canal pressure regulating device has a body, sized and shaped for insertion into the external ear canal of the person, the body having an orifice allowing for the communication of fluids in and out of the external ear canal with the device in place within the external ear canal. The device also has a sealing mechanism coupled to the body for sealing for the external ear canal from ambient. The device further has a pressure mechanism incorporated within the body and operably coupled to the orifice of the body for creating a selected pressure to be applied to the external ear canal with the device in place.

Preferably the external ear canal pressure regulating device further has a maintenance mechanism operably coupled to the orifice of the body for maintaining the selected pressure within the external canal with the body in place. Preferably the selected pressure within the external ear canal has a lower absolute value than the value of ambient pressure. Preferably the maintenance mechanism is a valve located within the orifice of the body. Preferably the valve is a one-way valve which only allows the fluid to pass from the external ear canal outwardly to ambient. Preferably the pressure mechanism is a bulbous portion of the body which when manually squeezed by the person restricts the volume of fluid present within the external ear canal with the body in place.

In an alternative embodiment the external ear canal pressure regulating device has a body, sized and shaped for insertion into the external ear canal of the person, the body has an orifice allowing for the communication of fluids in and out of the external ear canal with the device in place within the external ear canal. A first valve is positioned within the orifice of the body. The first valve is a one-way valve allowing for the passage of the fluid in only a first direction and a second valve positioned within the orifice of the body external to the first valve. The second valve is a one-way valve allowing for the passage of the fluid in only the first direction. The body has a bellows type wall at least one location between the first valve and the second valve such that manual manipulation of the body would temporarily cause the volume of fluid in the orifice between the first valve and the second valve to be reduced. In this way manual manipulation of the body will cause fluid to be transferred in the first direction to or from the external ear canal and the pressure caused by such transfer of the fluid to be maintained.

Preferably the first direction is outward creating a pressure in the external ear canal which has a lower value than the value of ambient pressure.

In an alternative embodiment the external ear canal pressure regulating device has a body, sized and shaped for insertion into the external ear canal of the person. The body has an orifice allowing for the communication of fluids in and out of the external ear canal with the device in place within the external ear canal. A valve is positioned within the orifice of the body. The valve is a one-way valve allowing for the passage of the fluid only into the external ear canal when the device is in place in the external ear canal. The body has a bellows type wall exterior of the valve. Thus, the manual squeezing of the bellows type wall of the body coupled with manual blockage of the orifice will cause the volume of fluid within the external ear canal to be increased and the pressure increase caused by such volume increase of the fluid to be maintained.

In an alternative embodiment the external ear canal pressure regulating device has a body, sized and shaped for insertion into the external ear canal of the person. The body has an interior and is capable of being manipulated allowing the interior of the body to vary in size. The body has a mechanism allowing the body to be manipulated so that the interior is made only larger. The manual manipulation of the body will cause fluid within the external ear canal to expand over a greater volume and causing the negative pressure in the external ear canal with respect to ambient created to be maintained.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
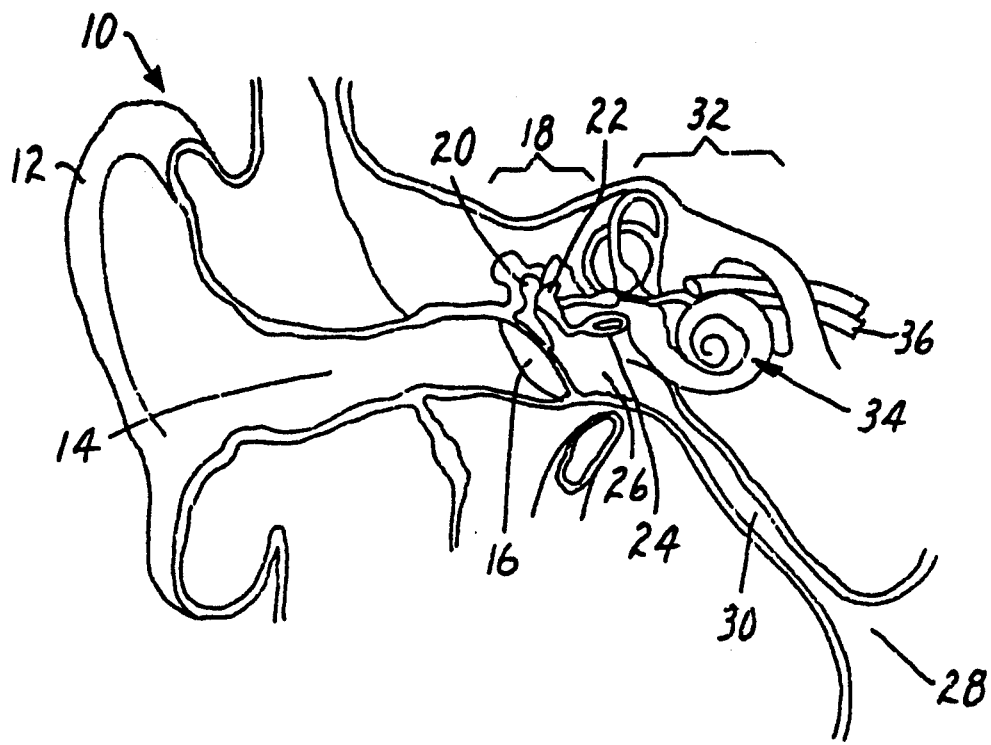
FIG. 1 is a cross-sectional view of the human ear.

FIG. 1 illustrates a cross-sectional view of the human ear 10 showing the pinna (auricle) 12, the external ear canal (external meatus) 14 and the tympanic membrane 16 (commonly called the ear drum). Auditory sounds in the environment enter the external ear canal 14 and acoustically vibrate the tympanic membrane 16. Ossicles 18 (also called the ossicular chain, and more particularly the malleous 20, the incus 22 and the stapes 24) are connected to the tympanic membrane 16 and transmit the acoustic vibrations representing the auditory sound through the middle ear space 26. The middle ear space 26 is vented to the nasopharynx 28 by the Eustachian tube 30. The ossicles 18 then transmit the vibrations to the inner ear 32, represented by the cochlea 34.

The cochlea 34 is a spiral, fluid-filled organ which transforms the acoustic vibrations into nerve discharges which are transmitted to the brain (not shown) by the VIIIth (eighth) nerve 36. The nerve discharges are recognized by the brain as the auditory sensation received by the external ear canal 14.

Figure 2:
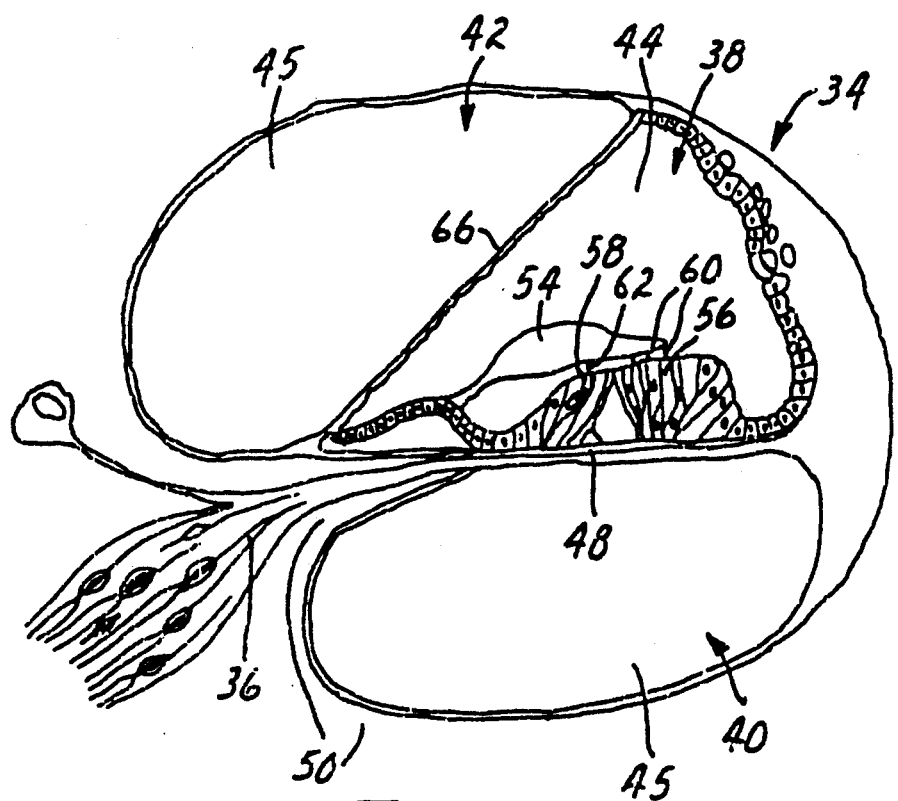
FIG. 2 is a cross-sectional view of the cochlea.

FIG. 2 illustrates the anatomy of the cochlea 34 by showing a cross-sectional view. The section of the cochlea 34 represented by the illustration of FIG. 2 shows the anatomy at one particular location around the spiral of cochlea 34. Other locations around the spiral would look similar but it is believed would be responsible for a different perceived frequency of sensation. The cochlea 34 is believed to be place-frequency sensitive, i. e., a place, or position, around the spiral is sensitive only to a particular frequency of sound sensation. It is also believed that the spiral of the cochlea 34 is sensitive to increasingly lower frequencies as the position along the spiral moves increasingly toward the apex of the cochlea.

The cross-section of the cochlea 34 is composed of three separate compartments, namely the scala media 38, the scala tympani 40 and the scala vestibuli 42. The scala media 38 is filled with a fluid 44 known as the endolymph. The scala tympani 40 and the scala vestibuli 42 are filled with a fluid 45 known as the perilymph. The outer two compartments, namely the scala tympani 40 and the scala vestibuli 42, communicate with each other at the apex of the cochlea 34. It is believed that the fluid 44 in the central compartment, namely the scala media 38, does not communicate with the fluid 45 in the two outer compartments, namely the scala tympani 40 and the scala vestibuli 42.

Figure 3:
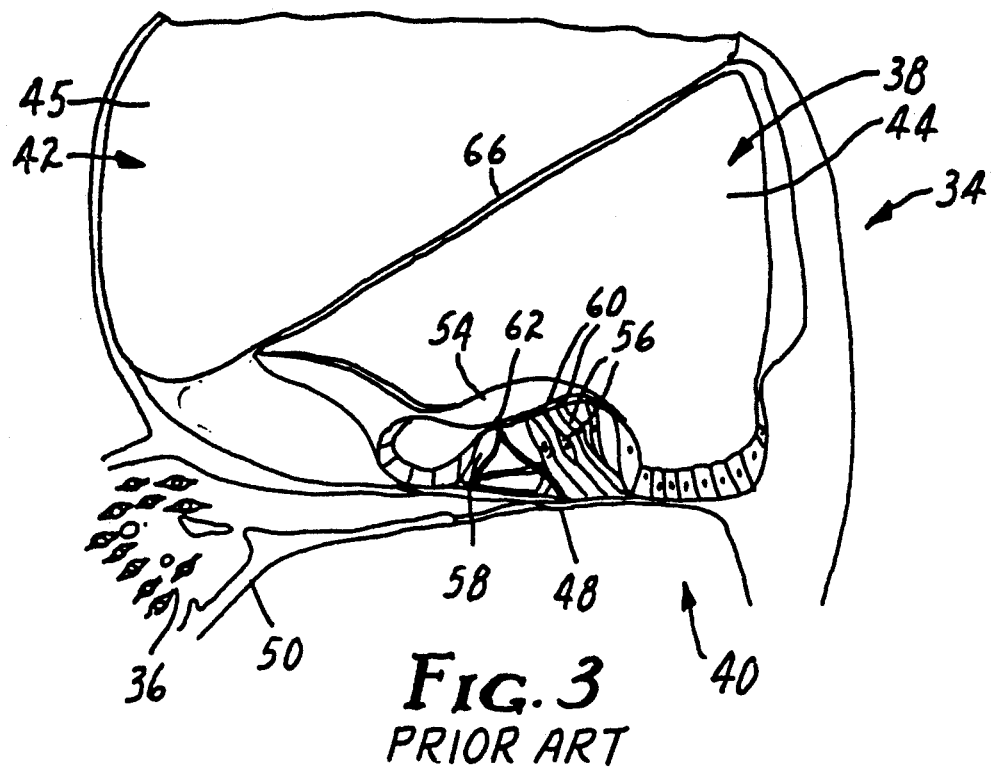
FIG. 3 is an expanded cross-sectional view of a portion of the cochlea.

Reference may now be had to FIG. 2 and to FIG. 3 which illustrate a portion of the cross-section of the cochlea 34 shown is expanded detail. The scala media 38 and the scala tympani 40 are shown as before. Separating the scala media 38 and the scala tympani 40 is the basilar membrane 48. The osseous spiral lamina 50 is bony in construction and not very flexible. The basilar membrane 48 is constructed of more flexible tissue. A gelatinous flap of tissue known as the tectorial membrane 54 extends into the scala media 38. There are four rows (represented by reference numerals 56 and 58) of hair cells within the scala media 38. Three rows of hair cells are referred to as the outer hair cells 56. The fourth row of hair cells are referred to as the inner row of hair cells 58.

Figure 4:
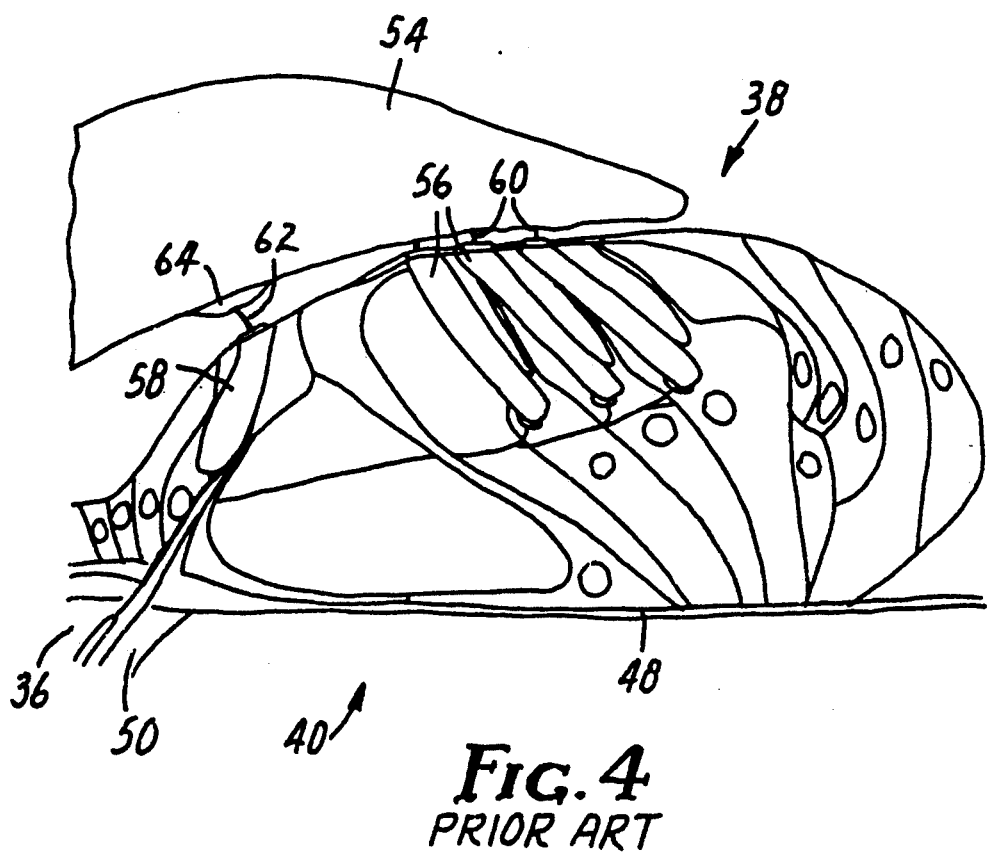
FIG. 4 is a cross-sectional view of a portion of a normally functioning cochlea.

The following description describes what is believed to be known about the normal functioning of the cochlea 34 and, hence, the normal functioning of the hearing of an individual. This can be explained by reference to FIGS. 2 and 3, just discussed, and by reference to FIG. 4 which illustrates a still further expanded view of a portion of the cochlea 34 showing the scala media 38, the scala tympani 40, the basilar membrane 48, and the relationship of the tectorial membrane 54 to the inner row of hair cells 58 and the outer hair cells 56. The inner row of hair cells 56 is the row of hair cells which is connected to the VIIIth nerve 36 and the row of hair cells which actually transduce auditory input into neural output thus producing auditory sensations. In an individual with normal hearing, the stereocilia 62 of the inner row of hair cells 58 is separated from the tectorial membrane 54 by a small fluid 44 space. The three rows of outer hair cells 56 whose stereocilia 60 are directly attached to the tectorial membrane 54 perform the broad function of transducing the mechanical energy contained in the oscillations of the fluid 44 in the scala media 38 into electrical energy and retransducing that electrical energy generated back into mechanical energy to provide amplification and to sharpen the tuning of the cochlea. The three rows of outer hair cells 56, by way of their associated stereocilia 60, also maintain a separation of the inner row of hair cells 58, and their associated stereocilia 62, from the tectorial membrane 54. The inner row of hair cells 56, which are strictly passive, then sense the amplified movement of the basilar membrane 48 and/or tectorial membrane 54 through shearing forces in the fluid 44 which causes deflection of their associated stereocilia 62, depolarization, and release of neurotransmitter which excites the VIIIth nerve 36.

Figure 5:
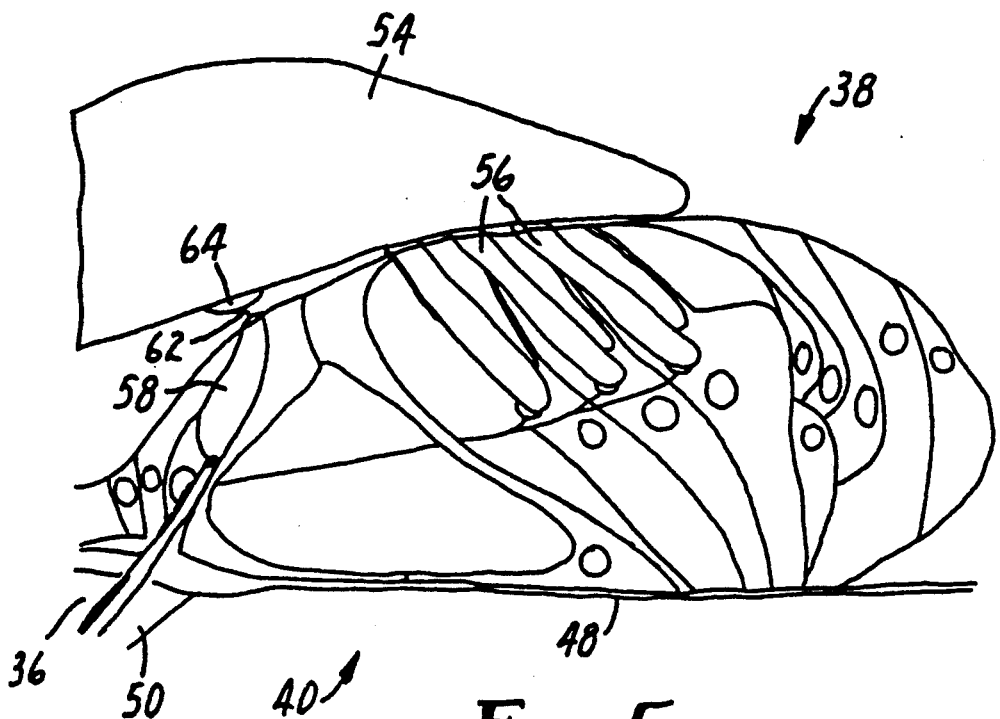
FIG. 5 is a cross-sectional view of a portion of a cochlea which has damaged stereocilia of the three rows of outer hair cells.

FIG. 5 is believed to illustrate a damaged cochlea 34 typical of the damage incurred by an individual having non-Meniere's induced tinnitus. In the cochleae 34 of persons with impaired hearing, particularly those damaged as a result of excessive noise, it is believed that the damaged and sometimes missing stereocilia 60 of the three rows of outer hair cells 56 may allow the tectorial membrane 54, at least at one location or along a portion of the cochlea 34, to contact the stereocilia 62 of the inner row of hair cells 58 causing deflection of the stereocilia 62, depolarization of the inner hair cells 58 and release of the neurotransmitter and, thus, excitation of the VIIIth nerve 36 resulting in the sensation of hearing when no sound is present, i. e., tinnitus.

Figure 6:
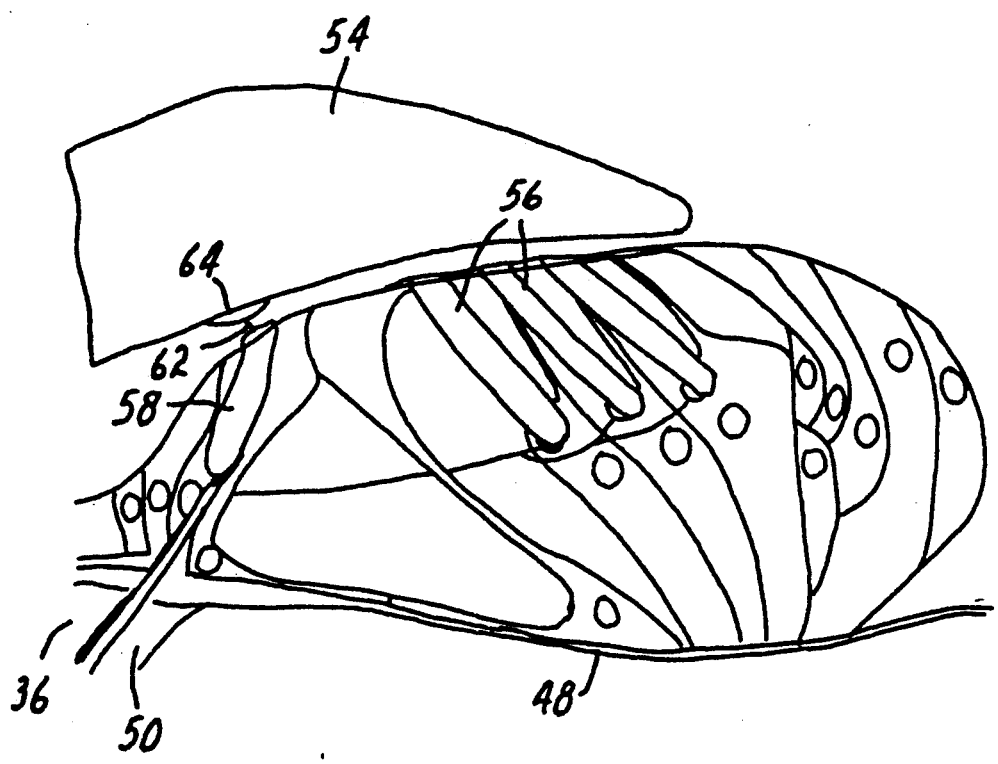
FIG. 6 is a cross-sectional view of the portion of the cochlea of FIG. 5 with a displaced basilar membrane.

FIG. 6 is believed to illustrate the damaged cochlea 34 of FIG. 5 which has been manipulated to reduce, i. e., suppress, or cure the tinnitus present. The cure, then, for the prevention or reduction in the sensation of hearing, and to alter other aspects of the auditory sensation, is to separate the tectorial membrane 54 from the stereocilia 62 of the inner row of hair cells 58 where contact has been made. It is believed that displacing the basilar membrane 48, especially a static displacement of the basilar membrane 48 in a direction toward the scala tympani 40 and away from the scala media 38, provides the desired separation of the stereocilia 62 of the inner row of hair cells 58 and results in the reduction or elimination of tinnitus. In the vast majority of cases involving non-Meniere's tinnitus it is believed to be desirable to reposition the basilar membrane 48 statically in a direction away from the scala media 38 and toward the scala tympani 40. As can be seen from FIG. 6, repositioning the basilar membrane 48 in this direction causes the tectorial membrane to reestablish its normal position with respect to the stereocilia 62 of the inner row of hair cells 58. With the tectorial membrane 54 repositioned, the tectorial membrane 54, especially Hensen's stripe 64, no longer deflects the stereocilia 62 of the inner row of hair cells 58 (in the absence of actual sound). Since the stereocilia 62 of the inner row of hair cells 58 are no longer chronically contacted by the tectorial membrane 54, the VIII nerve fibers at this location do not discharge excessively in the absence of actual sound and the sensation of tinnitus is completely eliminated. Of course, in an individual in which the exact proper repositioning cannot be achieved, repositioning toward the "normal" would result in a reduction or a suppression of the tinnitus. With the tectorial membrane 54 properly repositioned in its "normal" position, the normal functioning of the inner row of hair cells is reestablished. When vibrations are present in the fluid 44 of the scala media 38, the movement of the tectorial membrane 54 and/or basilar membrane 48 result in the deflection of the stereocilia 62 of the inner row of hair cells 58 located at the position (or location) along the cochlea 34 (and, hence, along the basilar membrane 48) which corresponds to the frequency of the vibrations resulting in the perception of hearing to the sound causing the vibration at that frequency.

Once present, the loss or damage to the outer hair cells 56 and their associated stereocilia 60 is a chronic condition. Similarly, the deflection of the stereocilia 62 of the inner hair cells 58 and the resulting tinnitus in this case is a persistent condition, which then suggests a static, or relatively invariant repositioning of the involved structures to achieve a suppression of the tinnitus. This repositioning preferably needs to vary at less than 20 Hertz, since rates above this would result in audible sensations and may defeat the purpose of the tinnitus suppression. Preferably, this repositioning should be relatively invariant such that the separation is maintained between the stereocilia 62 of the inner hair cells 58 and the tectorial membrane 54 for long periods of time, thereby suppressing the tinnitus. The longer the period of time that the structures are repositioned, the greater the duration of the tinnitus suppression. For example, low frequencies of repositioning (e.g. 1 Hertz) would be expected to achieve intermittent reduction of the tinnitus however a static, relatively invariant repositioning of the involved structures is preferable to achieve non-intermittent suppression of the tinnitus.

While it is believed to be desirable to reposition the basilar membrane 48 statically, such static repositioning may not absolutely required. It is believed preferable that the repositioning of the basilar membrane 48 be static since the underlying cause of the non-normal positioning of the basilar membrane 48 resulting in the tinnitus is relatively static. However, it is to be recognized and understood that other functions, generally not associated with the suppression of tinnitus, may dictate or suggest that the mechanisms associated with the repositioning of the basilar membrane (and, hence, the relationship of the tectorial membrane 54 to the inner row of hair cells) not be completely non-varying. For example, a basilar membrane repositioning mechanism could be utilized in conjunction with hearing enhancement mechanisms which may require the variation in the positioning of the basilar membrane. A hearing aid, acoustic or implanted, could be utilized along with the preferable relatively static repositioning of the basilar membrane 48 to create a combination of a relative static repositioning to suppress the tinnitus symptom of the patient's hearing and an amplification or other processing of auditory sensations resulting in variant signals and, hence, variant repositioning of the basilar membrane to achieve the hearing enhancement function of the mechanism.

It is believed that in the typical Meniere's disease patient the fluid pressure in the scala media 38 is higher than normal. This higher than normal pressure results in a deflection of the basilar membrane 48 toward the scala tympani 40 (and also a deflection of Reissner's membrane 66 toward the scala vestibuli 42), a condition known as hydrops. Since in the typical Meniere's disease, the outer row of hair cells 56 would not be damaged, it is thought that the deflection of the basilar membrane 48 could cause the tectorial membrane 54 to be pulled down by the outer row of hair cells 56 to which it would be attached and cause the tectorial membrane 54 to contact the inner row of hair cells 58 along a substantial portion of the cochlea 34 resulting in the typical low frequency roaring tinnitus associated with Meniere's disease. In this situation it may be desirable to reposition the basilar membrane 48 back to its normal position (in this case moving the basilar membrane 48 toward the scala media 38) to relieve the tectorial membrane from contacting the inner row of hair cells. The hydrops condition of Meniere's disease is a relatively static, i. e., relative to auditory sounds, signals or vibrations, condition. A static, relatively invariant, repositioning of the basilar membrane 48 would be preferable. It is believed that the repositioning should not vary substantially at a rate high enough which would result in audible sensations, otherwise the purpose of suppressing the tinnitus may be defeated. Generally, it is expected that the rate of change for the purpose of repositioning the basilar membrane 48 would be not more than 1 Hertz, or possibly not more than 20 Hertz.

It has been found that by modifying the ambient air pressure in the external ear canal 14, the tympanic membrane 16 may be repositioned resulting in a movement of the ossicles 18. The movement of the ossicles 18 results in a change in the pressure of fluid 45 in the cochlea 34. A decrease in the ambient air pressure in the external ear canal 14 causes an outward movement of the stapes 24 and a momentary decrease in the pressure of the fluid 45 in the outer chambers (40 and 42) of the cochlea 34 with a resulting momentary decrease in the pressure of fluid 44 in the scala media 38. A decrease in the ambient air pressure in the external ear canal 14 results in a repositioning of the basilar membrane 48 toward the scala tympani 40. This is believed to be the preferred direction of movement of the basilar membrane 48 to suppress tinnitus in patients having noise induced hearing loss, the most common cause of tinnitus.

Thus, it is believed that a change in ambient air pressure in the external ear canal 14 effects the desired repositioning of the basilar membrane 48. As in the case of repositioning the basilar membrane 48 directly, by supplying a selected amount of pressure decrease, preferably, or increase, if a pressure increase then preferably statically, it is believed that the basilar membrane 48 may be repositioned and the tectorial membrane 54 may be properly repositioned in its "normal" position. The normal functioning of the inner row of hair cells is then believed to be reestablished. It is believed that when vibrations are present in the fluid 44 of the scala media 38, the movement of the tectorial membrane 54 and/or basilar membrane 48 result in the deflection of the stereocilia 62 the inner row of hair cells 58 located at the position (or location) along the cochlea 34 which corresponds to the frequency of the vibrations resulting in the perception of hearing to the sound causing the vibration at that frequency.

As discussed before, once present, the loss or damage to the outer hair cells 56 and their associated stereocilia 60 is usually a chronic condition. Similarly, the deflection of the stereocilia 62 of the inner hair cells 58 and the resulting tinnitus in this case is usually a persistent condition, which then usually requires a static, or relatively invariant pressure change in the external ear canal 14 to achieve a suppression of the tinnitus. This repositioning preferably needs to vary at less than 20 Hertz, since rates above this would result in audible sensations and defeat the purpose of the tinnitus suppression. Preferably, this pressure change should be relatively invariant such that the separation is maintained between the stereocilia 62 of the inner hair cells 58 and the tectorial membrane 54 for long periods of time, thereby suppressing the tinnitus. The longer the period of time that the pressure change (relative to ambient) in the external ear canal 14, the greater the duration of the tinnitus suppression. For example, low frequencies of pressure change (e.g. 1 Hertz) would be expected to achieve intermittent reduction of the tinnitus however a static, relatively invariant pressure change in the external ear canal 14 is preferable to achieve non-intermittent suppression of the tinnitus.

While it is considered desirable to supply a static pressure decrease, preferably, or increase to the external ear canal 14, maintaining such a static pressure is not believed to be required. It is believed to be preferable that the pressure being supplied to the external ear canal 14 be static since the underlying cause of the tinnitus is relatively static. However, it is to be recognized and understood that other functions, generally not associated with the suppression of tinnitus, may dictate or suggest that the mechanisms associated with the pressures being supplied to the external ear canal 14 may not be completely invariant. For example, it is contemplated that apparatus of the present invention could be utilized in conjunction with hearing enhancement mechanisms which may require variations in the pressures being supplied to the external ear canal 14. A hearing aid could be utilized along with the apparatus of the present invention to create a combination of a relative static pressure to suppress the tinnitus symptom of the patient's hearing and an amplification or other processing of auditory sensations resulting in variant pressures and, hence, variant pressures in the external ear canal 14 to achieve the hearing enhancement function of the mechanism.

Figure 7:
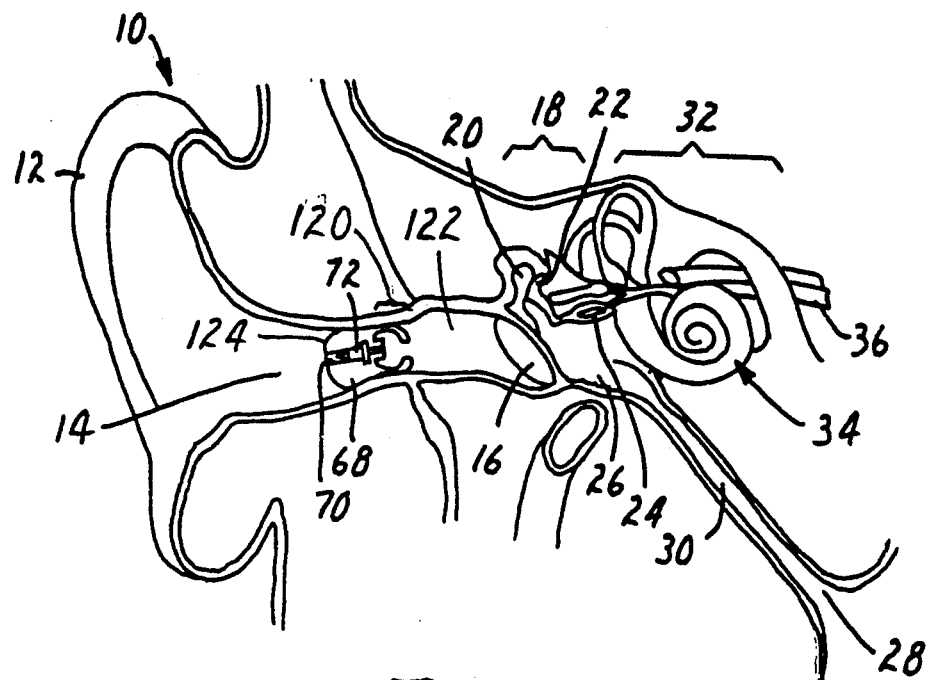
FIG. 7 is a cross-sectional view of a preferred embodiment of the apparatus of the present invention in place in the external ear canal of a patient.
Figure 8:
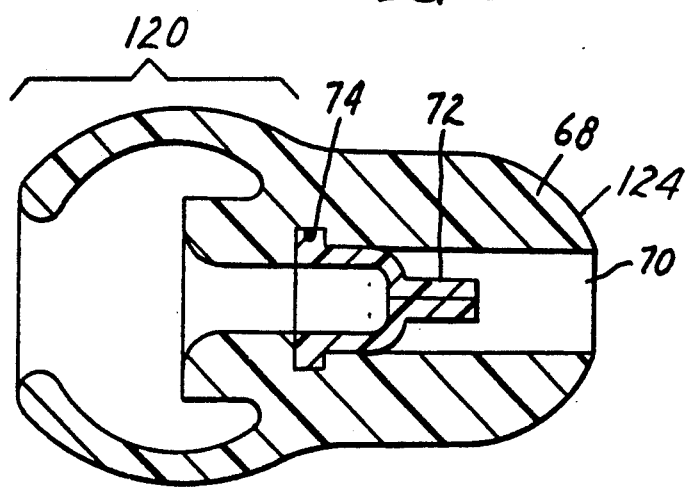
FIG. 8 is an enlarged sectional view of a preferred embodiment of the apparatus of the present invention.

FIG. 7 illustrates a preferred embodiment of the apparatus of the present invention in place in the external ear canal 14 of a patient. FIG. 8 is an illustration of the same apparatus shown in expanded cross-sectional form. An ear plug body 68 is shown inserted (in FIG. 7) into the external ear canal 14. The ear plug body has a bulbous portion 120 which is designed to intimately contact the wall of the external ear canal 14. The contact which the bulbous portion 120 makes with the wall of the external ear canal 14 seals the portion of the external ear canal 14 interior of the ear plug body 68 from the exterior ambient environment. Preferably the ear plug body 68 maintains a good seal with the wall of the external ear canal 14 to result in a substantially hermetic seal of the external ear canal 14 interior of the ear plug body 68. Ear plug body 68 has an orifice 70 passing through ear plug body 68 longitudinally allowing for the passage of fluids either into or out of the interior portion 122 of the external ear canal 14. It is preferred that the fluid passed, and utilized to modify the pressure in the interior portion of the external ear canal 14 be a gas, in particular, air. A valve 72 is fitted into a notch 74 of the orifice 70 of the ear plug body 68. It is preferred that valve 72 be a one-way valve, i. e., only allowing the passage of fluid substantially in a single direction. Since it is generally preferred that negative pressures be developed and maintained within the interior portion 122 of the external ear canal 14, it is preferred that valve 72 be oriented to allow fluid to pass only the the interior of the external ear canal 14 outwardly to ambient. In the embodiment of the apparatus illustrated in FIG. 8, the left end of the ear plug body 68 would be inserted into the external ear canal 14 and, hence, it is preferred that valve 72 be oriented to pass fluid only from left to right through the orifice 70.

In operation the apparatus is operated by grasping end 124 and inserting the ear plug body 68, bulbous portion 120 first, into the external ear canal 14. Once inserted valve 72 will substantially prevent fluid from passing into the interior portion 122 of the external ear canal 14 from ambient. The bulbous portion 120 may then be compressed by pressing upon end 124 of the ear plug body 68. As the bulbous portion 120 is compressed fluid is passed outwardly through valve 72 through orifice 70 to ambient. The end 124 may then be released allowing the bulbous portion 120 to re-expand to its original size. Since very little fluid can re-enter the interior portion 122 of the external ear canal 14 due to one-way valve 72, the fluid remaining in the interior portion 122 of the external ear canal 14 will be at a reduced (lower) pressure than ambient.

If a greater pressure differential than that which can be achieved upon a single compression the bulbous portion 120 is desired, then end 124 can be repeatedly pressed and released until the desired pressure differential, or in the case of operation by the patient, until the desired relief from tinnitus, is achieved. Similarly, the amount of pressure differential achieved by a single operation can be varied by adjusting the amount by which end 124 is pressed. Typically it is expected that a pressure differential of 500 decaPascals can be created with a single operation. Typically it is expected that the bulbous portion 120 should provide sealing to the interior portion 122 of the external ear canal 14 for approximately 1,000 decaPascals.

The amount of pressure that can be induced in the interior portion 122 of the external ear canal 14 is inherently limited by the design of device. This provides an inherent safety feature which prevents the patient from creating an excessive pressure within interior portion 122 of the external ear canal 14 which would otherwise damage the tympanic membrane 16. First, the volume of fluid contained in the bulbous portion 122 compared with the volume of fluid contained in the interior portion 122 of the exterior ear canal 14 limits the pressure which can be achieved. Even if the bulbous portion were completed compressed, so that it had zero volume, there still would be some fluid contained in the interior portion 122 of the exterior ear canal 14. Hence, the amount of pressure created with a single compression is limited. Further, the strength of the material forming the bulbous portion 120 limits the overall pressure which is achievable since in order to create additional pressure the bulbous portion must be strong enough to re-expand following compression.

Of course, if it were desired, valve 72 could be inserted into the orifice with the opposite orientation, allowing fluid to pass only inwardly from ambient into the interior portion 122 of the external ear canal 14, creating only positive pressures with respect to ambient.

Figure 9:
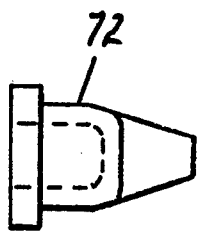
FIG. 9 is a side view of the valve used in the apparatus of FIG. 8.

An example for ear plug body 68 is constructed from a silicone rubber. In early tests with this ear plug body 68 a tip, model 12-2376-9592-4 Universal Soft Ear Tip available from Minnesota Mining and Manufacturing Company of St. Paul, Minn. from a stethoscope has been utilized with modifications. Ear plug body 68 has orifice 70 running longitudinally through it. A notch 74 is provided along orifice 70 to allow for easy insertion of valve 72. In a preferred embodiment, valve 72, illustrated in FIG. 9, is a duckbill valve, such as model VA 3426 available from Vernay Laboratories, Inc., of Yellow Springs, Ohio.

Figure 10:
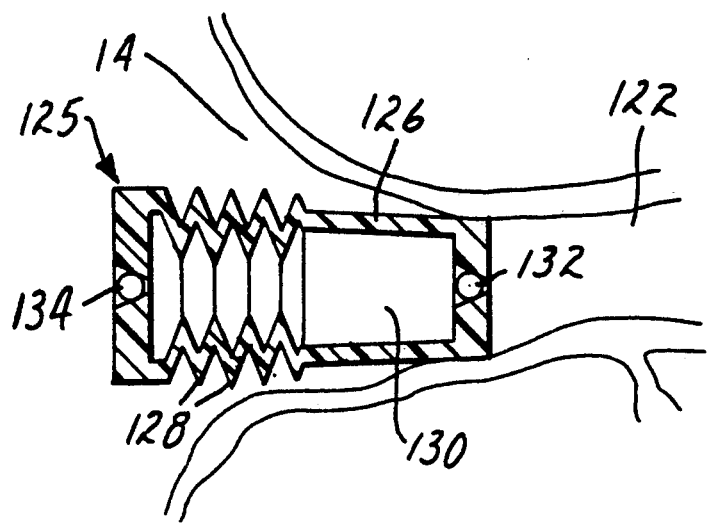
FIG. 10 is a diagrammatic view of an alternative embodiment of an external ear canal pressure regulating device of the present invention using two valves.

FIG. 10 illustrates an alternative embodiment of an apparatus 125 constructed according to the teaching of the present invention. A body 126 having a bellows type wall 128 is shown inserted into the external ear canal 14 of a patient. The body 126 has interior chamber 130 which communicates both toward the interior portion 122 of the external ear canal 14 and toward the exterior of the external ear canal 14, namely ambient. A first valve 132 is located in the passage between the interior chamber 130 and the interior portion 122 of the external ear canal. A second valve 134 is located in the passage between the interior chamber 130 and the exterior of the external ear canal 14. Both valves 132 and 134 are one-way valves and both are oriented to allow the passage of fluid in the same direction, e. g. from left to right in the illustration, only. Although shown as simple ball valves in FIG. 10, it is preferred that valves 132 and 134 be constructed similarly to the duck bill valve 72 already described with reference to FIGS. 7, 8 and 9.

In operation, the external ear canal pressure regulating device 125 illustrated in FIG. 10 can be grasped at the end nearest valve 134 and inserted into the external ear canal 14 of the patient opposite end, i. e., the end nearest valve 132, first. The end nearest valve 134 can then be pressed, at least partially collapsing the bellows type wall 128 and causing the volume of fluid contained in interior chamber 130 to be made smaller. The fluid in interior chamber 130 will be at least partially expelled, due to the increase in pressure due to the decreased volume, through one of the valves 132 or 134. With the preferred embodiment of valves 132 and 134 being oriented to pass fluid only from left to right in the Figure, i. e., from interior to exterior with respect to the interior portion 122 of the external ear canal 14, the fluid would be expelled through valve 134 to ambient. The end of the device can then be released and the bellows type wall 128 will re-expand to near its original shape allowing interior chamber 130 to regain its original volume. As interior chamber 130 increases in volume, the pressure of the fluid in interior chamber 130 decreases, drawing fluid in through valve 132 from the interior portion 122 of the external ear canal 14. Since fluid is removed from the interior portion 122 of the external ear canal 14, the pressure of the fluid in the interior portion 122 is decreased. Of course, with valves 132 and 134 in reversed orientation, fluid would pass from right to left in the Figure, i. e., from ambient to the interior portion 122 of the external ear canal 14, increasing the pressure in the interior portion 122.

Figure 11:
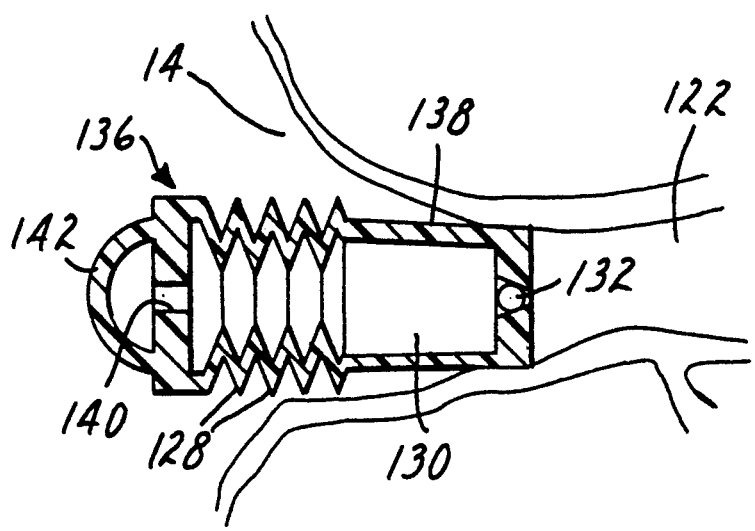
FIG. 11 is a diagrammatic view of an alternative embodiment of an external ear canal pressure regulating device of the present invention using a single valve.

FIG. 11 illustrates an alternative embodiment of an external ear canal device 136 which is similar to the device 125 illustrated in FIG. 10. In the device 136 of FIG. 11 only a single valve 132 is utilized, preferably valve 132 is oriented to pass fluid only from left to right in Figure, i. e., from the interior portion 122 of the external ear canal to the interior chamber 130 of the body 138. Body 138 is similar to body 126 but instead in utilizing valve 134, body 138 has an orifice 140 allowing for the communication of fluid between interior chamber 130 and ambient. In operation, handle 142 is grasped and the end of the device with valve 132 is inserted into the external ear canal 14. Handle 142 may be pushed, collapsing the bellows type wall 128. The user may then cover orifice 140, for example with a finger, and allow the bellows type wall 128 to re-expand the interior chamber 130. As interior chamber 130 expands, fluid is drawn through valve 132 from the interior portion 122 of the exterior ear canal decreasing the pressure there. Of course, if valve 132 were oppositely oriented and orifice 140 were closed during compression, then a pressure increase would be achieved within the interior portion 122 of the external ear canal 14.

Figure 12:
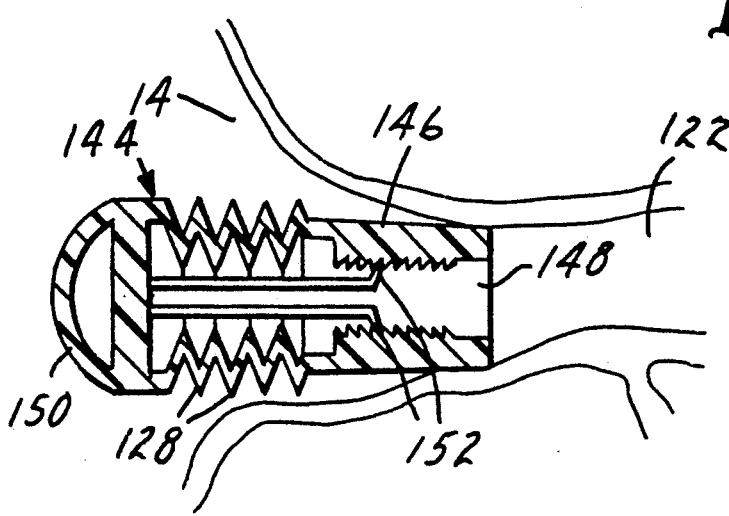
FIG. 12 is a diagrammatic view of an alternative embodiment of a valveless external ear canal pressure regulating device of the present invention.

FIG. 12 illustrates another alternative embodiment of an external ear canal pressure regulating device 144 of the present invention. Device 144 has a body 146 forming an interior chamber 148 which is open to the interior portion 122 of the external ear canal 14. Body 146 has a bellows type wall 128 similar to body 126 of the device 125 illustrated in FIG. 10. A handle 150 is located at the exterior end of the device 144 to allow grasping and pulling. A ratchet mechanism 152 is provided which will enable the body 146 to retain a selected shape to stabilize the volume of interior chamber 148. No valves are needed.

In operation, the device 144 of FIG. 11 is grasped by the handle 150 and inserted into the external ear canal 14 of the patient. Once body 146 is positioned snugly against the wall of the external ear canal 14 sealing the interior portion 122 from ambient, handle 150 may be grasped and either pushed or pulled and, hence, either decreasing or increasing, respectively, the volume of interior chamber 148 and either increasing or decreasing, respectively, the pressure of the fluid contained in the interior portion 122 of the external ear canal 14. Ratchet mechanism 152 then maintains that position and pressure in the ear canal.

Figure 13:
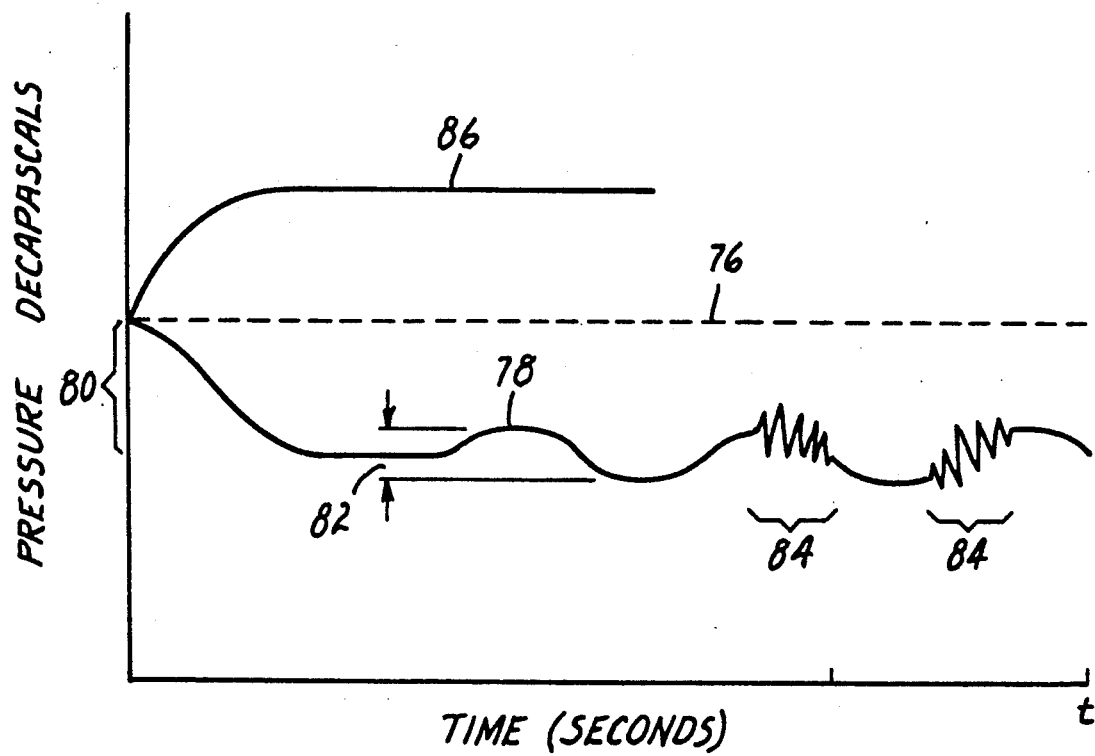
FIG. 13 is a chart of the exemplary pressures which can be used in conjunction with the apparatus and method of the present invention.

FIG. 13 illustrates exemplary pressures, relative to ambient 76, which may achieved in accordance with the present invention. The ordinate of the graph shown in FIG. 13 represents time (in seconds) and the abscissa represents pressure (in decaPascals). Ambient pressure 76 is shown as a dashed line. In accordance with the present invention, line 78 illustrates a change in pressure, e. g. a decrease in pressure, in the external ear canal 14 interior of ear plug body 68. This pressure decrease is, preferably, maintained relatively constant. Generally this pressure is expected to be maintained over the major portion of the treatment of the tinnitus, although some residual improvement in, i. e., suppression of, tinnitus has been observed following the elimination of the pressure change. Generally, it is expected that the pressure change 80 in the interior portion 122 of the external ear canal 14 expected to accomplish the suppression of tinnitus is to be in the range of 400–600 decaPascals, again preferably a pressure decrease as shown by line 78, although smaller and greater have been known to accomplish some suppression or be required to achieve complete suppression of the tinnitus. Pressure changes 80 up to 1,000 decaPascals have been utilized. It is expected that, in some individuals, greater pressure changes 80 might be tolerable or desirable. At some point, pressure on the tympanic membrane 16 becomes so great that intense pain is experienced militating against its use as a tinnitus suppression mechanism. In order to maintain the preferably static pressure changes illustrated by line 78, it is preferred that the general variation 82 in the pressure change be not more than 10 percent of the total pressure change 80. Generally, since it is desired that the general variation 82 in the pressure not interfere with the auditory sensation, it is preferred that the variation 82 not vary a rate which results in a frequency which is auditory. It is preferred that the variation if any, occur at a rate not more than 1 Hertz, and still preferably not more than 20 Hertz. It is to be recognized that the preferably static pressure change 80 can be utilized in conjunction with other auditory related pressures in the external ear canal 14 associated with improving hearing or ameliorating hearing deficiencies and can be in addition, although not directly related, to the pressure change 80. These additional pressures are represented in the graph of FIG. 10 by the changes in pressure indicated by reference numeral 84. Line 86 in the graph of FIG. 13 is representative of the situations where it is desirable to have an increased pressure in the external ear canal 14 in order to suppress tinnitus. With the increased pressure represented by line 86, it is preferred that the pressure be static, i. e., relatively invariant.

Thus, it can be seen that there has been shown and described a novel apparatus and method for suppressing tinnitus. It is to be recognized and understood, however, that various changes, modifications and substitutions in the form and the details of the present invention may be made by those skilled in the art without departing from the scope of the invention as defined by the following claims.

We claimed:

1. A tinnitus suppression device adapted to be utilized in conjunction with a person having an auditory system with an external ear canal, said tinnitus suppression device comprising:
   a body, sized and shaped for insertion into said external ear canal of said person, said body having an orifice allowing for the communication of fluids in and out of said external ear canal;
   sealing means coupled to said body for sealing said external ear canal from ambient; and
   pressure means incorporated within said body and operably coupled to said orifice of said body for creating a selected negative pressure, with respect to ambient, to be chronically applied to said external ear canal with said device in place;
   whereby said tinnitus suppression device creates said selected negative pressure within said external ear canal suppressing said tinnitus.

2. A tinnitus suppression device as in claim 1 which further comprises maintenance means operably coupled to said orifice of said body for maintaining said selected pressure within said external canal with said body in place.

3. A tinnitus suppression device as in claim 2 wherein said maintenance means comprises a valve located within said orifice of said body.

4. A tinnitus suppression device as in claim 3 wherein said valve is a one-way valve which only allows said fluid to pass from said external ear canal outwardly to ambient.

5. A tinnitus suppression device as in claim 2, wherein said pressure means comprises a bulbous portion of said body which when manually squeezed by said person lowers the volume of fluid present within said external ear canal and said body with said body in place and which when manually released lowers the pressure of said fluid still present in said external ear canal with respect to ambient.

6. A tinnitus suppression device as in claim 5 wherein said pressure is lowered by approximately 500 decaPascals.

7. A tinnitus suppression device adapted to be utilized in conjunction with a person having an external ear canal, said tinnitus suppression device comprising:

an ear plug adapted to be placed in said external ear canal of said person, said ear plug having an orifice allowing for the communication of fluids in and out of said external ear canal with said ear plug in place within said external ear canal; and pressure means incorporated within said ear plug and operably coupled to said orifice of said ear plug for creating a selected negative pressure, with respect to ambient, to be chronically applied to said external ear canal with said ear plug in place;

whereby said device creates said selected negative pressure within said external ear canal suppressing said tinnitus.

8. A tinnitus suppression device as in claim 7 which further comprises maintenance means operably coupled to said orifice of said ear plug for maintaining said selected pressure within said external canal with said ear plug in place.

9. A tinnitus suppression device as in claim 8 wherein said maintenance means comprises a valve located within said orifice of said ear plug.

10. A tinnitus suppression device as in claim 9 wherein said valve is a one-way valve which only allows said fluid to pass from said external ear canal outwardly to ambient.

11. A tinnitus suppression device as in claim 10 wherein said pressure means comprises a bulbous portion of said ear plug which when manually squeezed by said person restricts the volume of fluid present within said external ear canal with said ear plug in place.

12. A tinnitus suppression device as in claim 11 wherein said pressure is lowered by approximately 500 decaPascals.

13. A tinnitus suppression device adapted to be utilized in the external ear canal of a person, said device comprising:

sealing means, sized and shaped for insertion into said external ear canal of said person, said sealing means having an orifice allowing for the communication of fluids in and out of said external ear canal with said device in place within said external ear canal for sealing said external ear canal from ambient;

pressure means incorporated within said device and operably coupled to said orifice of said sealing means for creating a selected negative pressure, with respect to ambient, to be chronically applied to said external ear canal with said device in place; and maintenance means operably coupled to said orifice for maintaining said selected negative pressure in said external ear canal;

whereby said device creates and maintains said selected negative pressure within said external ear canal suppressing said tinnitus.

14. A tinnitus suppression device as in claim 13 wherein said maintenance means comprises a valve located within said orifice.

15. A tinnitus suppression device as in claim 14 wherein said valve is a one-way valve which only allows said fluid to pass from said external ear canal outwardly to ambient.

16. A tinnitus suppression device as in claim 15 wherein said pressure means comprises a bulbous portion of said device which when manually squeezed by said person reduces the volume of fluid present within said external ear canal with said device in place.

17. An external ear canal pressure regulative device adapted to be utilized in conjunction with the external ear canal of a person, said device comprising:

a body, sized and shaped for insertion into said external ear canal of said person, said body having an orifice allowing for the communication of fluids in and out of said external ear canal with said device in place within said external ear canal;

sealing means coupled to said body for sealing said external ear canal from ambient; and pressure means incorporated within said body and operably coupled to said orifice of said body for creating a selected negative pressure, with respect to ambient, to be chronically applied to said external ear canal with said device in place;

whereby said tinnitus suppression device creates said selected negative pressure within said external ear canal suppressing said tinnitus.

18. An external ear canal pressure regulating device as in claim 17 which further comprises maintenance means operably coupled to said orifice of said body for maintaining said selected pressure within said external canal with said body in place.

19. An external ear canal pressure regulating device as in claim 18 wherein said maintenance means comprises a valve located within said orifice of said body.

20. An external ear canal pressure regulating device as in claim 19 wherein said valve is a one-way valve which only allows said fluid to pass from said external ear canal outwardly to ambient.

21. An external ear canal pressure regulating device as in claim 20 wherein said pressure means comprises a bulbous portion of said body which when manually squeezed by said person reduces the volume of fluid present within said external ear canal with said body in place.

22. An external ear canal pressure regulating device adapted to be utilized in conjunction with the external ear canal of a person, said device comprising:

a body, sized and shaped for insertion into said external ear canal of said person, said body having an orifice allowing for the communication of fluids in and out of said external ear canal with said device in place within said external ear canal;

a first valve positioned within said orifice of said body, said first valve being a one-way valve allowing for the passage of said fluid in only a first direction; and a second valve positioned within said orifice of said body external to said first valve, said second valve being a one-way valve allowing for the passage of said fluid in only said first direction;

said body having a bellows type wall at least one location between said first valve and said second valve such that manual manipulation of said body would temporarily cause the volume of fluid in said orifice between said first valve and said second valve to be reduced; wherein said first direction is outward whereby manual manipulation of said body will cause fluid to be transferred in said first direction to or from said external ear canal and the lower pressure caused by such transfer of said fluid to be maintained.

23. An external ear canal pressure regulating device adapted to be utilized in conjunction with the external ear canal of a person, said device comprising:

a body, sized and shaped for insertion into said external ear canal of said person, said body having an interior open to the interior portion of said external ear canal and being capable of being manipulated allowing said interior of said body to vary in size;

said body having mechanical means for allowing said body to be manipulated so that said interior is made only larger;

whereby manual manipulation of said body will cause fluid within said external ear canal to expand over a greater volume and causing the negative pressure in said external ear canal with respect to ambient created to be maintained.

* * * * *